United States Patent
Koop et al.

(10) Patent No.: US 6,413,253 B1
(45) Date of Patent: *Jul. 2, 2002

(54) SUBSURFACE HEATING OF MATERIAL

(76) Inventors: Dale E. Koop, 746 Southview Way, Woodside, CA (US) 94062; David R. Hennings, 11802 Kemper Rd., Auburn, CA (US) 95603

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/185,490

(22) Filed: Nov. 3, 1998

Related U.S. Application Data
(60) Provisional application No. 60/055,927, filed on Aug. 16, 1997.

(51) Int. Cl.[7] ............................................. A61B 18/04
(52) U.S. Cl. .............................. 606/27; 606/9; 606/10; 606/13; 607/88; 607/90; 607/96
(58) Field of Search .................................. 606/9–13, 20, 606/22, 23, 27, 28, 31, 41, 32, 33, 34; 607/88–94, 96, 101, 102

(56) References Cited

U.S. PATENT DOCUMENTS

| | | | |
|---|---|---|---|
| 3,821,510 A | 6/1974 | Muncheryan | |
| 4,733,660 A | 3/1988 | Itzkan | |
| 4,976,709 A | 12/1990 | Sand | |
| 5,020,995 A | 6/1991 | Levy | |
| 5,057,104 A | 10/1991 | Chess | |
| 5,098,428 A | 3/1992 | Sandlin et al. | |
| 5,137,530 A | 8/1992 | Sand | |
| 5,217,455 A | 6/1993 | Tan | |
| 5,304,169 A | 4/1994 | Sand | |
| 5,344,418 A | 9/1994 | Ghaffari | |
| 5,374,265 A | 12/1994 | Sand | |
| 5,484,432 A | 1/1996 | Sand | |
| 5,752,949 A | * 5/1998 | Tankovich et al. | 606/9 |
| 5,810,801 A | 9/1998 | Anderson et al. | |
| 5,814,008 A | * 9/1998 | Chen et al. | 604/21 |
| 5,814,040 A | * 9/1998 | Nelson et al. | 606/9 |
| 5,820,626 A | 10/1998 | Baumgardner | |
| 5,885,274 A | * 3/1999 | Fullmer et al. | 606/9 |
| 5,944,748 A | * 8/1999 | Mager et al. | 607/88 |
| 5,968,034 A | * 10/1999 | Fullmer et al. | 606/9 |

FOREIGN PATENT DOCUMENTS

EP        0043447 A2    6/1981

OTHER PUBLICATIONS

Spatially selective photocoagulation of biological tissues: feasibility study utilizing cryogen spray cooling, Applied Optics; vol. 35, No. 19; Anvarie et al., Jul. 1, 1996, 9 pages.

(List continued on next page.)

*Primary Examiner*—Linda C. M. Dvorak
*Assistant Examiner*—David M. Ruddy
(74) *Attorney, Agent, or Firm*—Ray K. Shahani, Esq.; Robert D. Fish, Esq.

(57) ABSTRACT

A method and system of delivering energy to material in which energy is converted to thermal energy in the material, and prior to significant therapeutic or other physiological change in a selected or target region of the material, results in a temperature rise which is maximum in a selected region of the material but which is insufficient to cause significant therapeutic or other physiological effect, the system for selective preheating of subsurface target regions of material such as human tissue including an energy source to preheat the material or tissue, a passive or active cooling means, and a device for delivering therapeutic or treatment energy, such as pulsed, electromagnetic, laser or non-coherent energy, to tissue during or after the preheating and cooling of the tissue.

5 Claims, 3 Drawing Sheets

OTHER PUBLICATIONS

Anvari et al, Spatially Selective Cooling of Biological Tissues: Application for thermally Medicated Therapeutic Procedures. Phys. Med. Bio. 40 (1995)241–252.

Anvari et al., Spatially Selective Photocoagulation of Biological Tissues: A Feasibility Study Utilizing Cryogen Spray Cooling. App. Optics, in press as of Jan. 8, 1996.

Duqye et al., Abstract 187: "Long Pulsed Ruby Laser for Hair Removal; Comparison b/w Different Spot Sizes, Temperatures and Interval b/w First and Second Treatment", Lasers in Surgery and Medicine, Proceedings of the American Society for Laser Medicine and Surgery 18th Annual Meeting in San Diego, California, Apr. 5–7, 1998.

Jenoptik Laserdiode GmbH product information: Actively cooled diode laser stack specification sheet, part No. 20282126 schematic etc., 4 pages.

Kincade, K., New Procedure Push Tissue Studies Beneath the Surface, Laser Focus World, 57–63 (Aug. 1995).

Omega Micro INfrared Temperature Transducer OS40 Series. Omega Complete Temperature Measurement Handbook and Encyclopedia (a registered mark), vol. 28, pages cover, J–45 and J–46 (1992).

Reliant Technologies Inc., Accu–Scan. Product News, Jan. 25, 1995, 2 pages.

Handpiece Extender Brochure, Spectrum Medical Technologies, Inc., RD 1100,RD 1200, 2 pages.

* cited by examiner

SUBSURFACE HEATING OF MATERIAL

The application claims benefit to Provisional application Ser. No. 60/055,927 filed Aug. 16, 1997.

FIELD OF THE INVENTION

The invention relates to a method and system of delivering energy to material such that the energy is converted to thermal energy in the material and results in a temperature rise which is maximum in a selected region of the material prior to treatment of the selected region to affect therapeutic or other physiological effect.

BACKGROUND OF THE INVENTION

It is sometimes desirable to cause heat affected changes in a selected portion inside of material, such as living tissue, without causing heat affected changes in portions that lie on either side of the heat affected portion.

Early attempts to use thermal energy to cause useful changes in collagen in attempts to perform thermalkeratoplasty and produce beneficial changes to the curvature of the cornea of the eye relied on heating layers of the cornea. External surface probes were used to apply heat, but resulted in several undesirable problems including epithelial thinning, stromal scarring, necrosis, and lack of reproducibility. Later, microelectrodes were used to apply heat at a set depth and time. Problems of scarring and ulceration were observed. Photothermalkeratoplasty using lasers to apply energy evenly into the stroma without excessive heating of the epithelial layer has been described. Laser energy at wavelengths near 2.6 $\mu$m or 3.9 $\mu$m were predicted to be efficacious for the procedure. Researchers described a method of cooling the surface layer to affect a beneficial temperature gradient and result in the desired temperature profile after the prescribed application of laser energy.

In 1992 the first use of a pulsed carbon dioxide laser for resurfacing of skin was reported. Skin tightening was discovered as a beneficial side affect of the procedure. The laser was designed to vaporize tissue water by rapid temperature elevation of directly irradiated tissue. The pulse duration was restricted to limit the spread of thermal energy to underlying tissue by conductive heat loss. The thermal profile of tissue after adjacent tissue has been vaporized varies from near 100° C. at the surface to near 37° C., body temperature, several millimeters below the surface. Desirable treatment of collagen occurs at temperatures near the range of 60° C. and 70° C. so there is a portion of tissue which reaches this temperature range during laser resurfacing, however, the surface layer or portion reaches temperatures which result in tissue necrosis.

Laser based photoepilation has been the object of study since the advent of the laser. It has been know for several years that optical pulses of the appropriate wavelength, pulse duration, and energy density impinging upon human skin will result in significant and enduring hair loss. The accepted theory for this phenomenon is that the penetration of the laser into the skin and its subsequent scattering results in heating of the hair shafts and follicles through selective absorption by melanin. The absorption of the radiation leads to heating of the follicle and subsequent thermal necrosis.

It has been found that for effective photoepilation to occur the energy must be penetrate approximately 3 mm into the tissue. Prevailing thought indicates that this means the absorption should occur in the melanin and not the oxyhemoglobin, thereby heating the regions around the hair follicle instead of heating the blood and blood vessels. Energy absorption in the melanin leads to elimination of the hair and the reduction or elimination of the ability of follicle to produce hair. Based on the absorption spectrum of melanin and oxyhemoglobin the wavelengths in the neighborhood of 700 nm have been thought to be efficacious. Therefore the Ruby laser at 694 nm, the Alexandrite laser around 760 nm, and flashlamps with emission spectrum centered near 700 nm have been used for this application. The aforementioned lasers are very inefficient, requiring high voltages, large supplies of cooling water. In addition, delivery of the energy to the skin surface is problematic due to the energy required for photoepilation. The pulse energies often exceed damage thresholds of delivery systems or are difficult channel to from the laser to the skin. The flashlamps themselves are inefficient, emit in all directions making efficient energy delivery difficult, and the flashlamps can be cumbersome to use in a handheld device. The convenient and controlled delivery of the optical energy of the appropriate wavelength, fluence and pulse duration to the skin surface for photoepilation in an efficient device has been difficult.

Attempts to cause thermal affected changes in collagen without vaporization or damage to the epithelial layers have met with difficulties. Additionally, most of the method of applying electromagnetic energy to materials such as tissue result in temperature increases which are greater at the surface. Methods to limit the rise in surface temperature by applying lower levels of energy result in heating deeper portions of tissue because a longer time of exposure is required to conduct thermal energy into deeper layers. Methods to minimize surface temperature elevations by using energy sources which have low absorption in the top layer of tissue also result in insufficient or inefficient heating, since these forms of energy generally have lower absorption in the underlying areas also. Attempts to cool the surface in order to limit the temperature rise at the surface, however, result in an increased energy requirement for subsurface heating, which must overcome the incidental subsurface cooling.

Attempts to treat specifically targeted regions within tissue, such as vascular tissue or melanin-containing tissue surrounding hair follicles, have resulted in undesirable temperature elevation in the tissue surrounding the targeted tissue. Utilization of cooling devices, passive as well as dynamic, have been effective in removing heat from surface tissue as well as the tissue surrounding the targeted tissue. However, the subsequent or simultaneous therapeutic treatment to be performed on the target tissue requires delivery of additional energy due to the inevitable cooling of the targeted tissue by the cooling device. The resulting net increase in treatment energy required, therefore, may not only interfere with the efficacy of the cooling device utilized but may also place a greater demand on the treatment energy source.

ADVANTAGES AND SUMMARY OF THE INVENTION

It is therefore an advantage of this invention to provide an improved system for creating selective temperature profiles in material such as tissue.

It is a further advantage of this invention to provide such a system which utilizes energy with an efficacious absorption coefficient in tissue.

It is a further advantage of this invention to provide such a system which selectively preheats a subsurface region within the tissue to be therapeutically or otherwise physiologically treated.

It is a further advantage of this invention to reduce the level of pulsed energy needed for treatment of the target portions of tissue by preheating the target portions of tissue.

It is a further advantage of this invention to provide such a system which selectively heats a subsurface layer in tissue to cause thermal affected changes in underlying layers of tissue.

It is a further advantage of this invention to provide such a system which selectively heats a subsurface region in skin tissue to cause thermal affected changes in selected regions of the skin without significant heat damage to surrounding regions.

It is a further advantage of this invention to provide such a system which selectively heats a subsurface region in tissue to cause a temperature profile which results in thermal affected changes in the selected region without undesirable thermal affected changes in portions surrounding the selected region.

It is a further advantage of this invention to provide such a system which selectively heats a subsurface portion in tissue to cause collagen shrinkage or collagen regeneration in skin.

It is a further advantage of this invention to provide such a system which selectively heats a subsurface region of vascular tissue.

It is a further advantage of this invention to provide such a system which selectively heats a subsurface region of tissue which contains portions of hair follicles.

In the preferred embodiments, the system for generating treatment energy contains a pulsed energy source, such as a solid-state laser, a neodymium-doped yttrium-aluminum-garnet (Nd:YAG) laser, a gas discharge flashlamp, a filament lamp, or an electrical current source.

In a preferred embodiment, energy from the system may be provided through a delivery device, such as but not limited to an optical fiber or fiber bundle or articulated arm for transmitting the light energy to tissue, or a electrically conductive applicator for delivering electrical energy to tissue.

The pulsed energy may be focused on tissue with a focusing lens or system of lenses.

The tissue may be preheated with any operative heating device such as, but not limited to, any intense light source, a gas discharge or other flashlamp, a filament or other incandescent lamp, a laser diode or other laser source, electrical current, probe or conductor, radiofrequency waves, microwaves, ultrasound or other source of electromagnetic energy which penetrates into regions of tissue, by conduction or convection as with a forced air blower, contact device, active or passive heating means, etc., beneath the surface such that the preheating occurs simultaneously with or just prior to the pulsed treatment application of energy from the energy delivery device, thus preferentially preheating a region of tissue without excessive or otherwise undesirable heating of or effect on surrounding tissue.

Material preheating may be accompanied by, at any time either prior to, concurrently with or subsequent to surface cooling, which may be accomplished using either passive or active heat sink or cooling means, to elevate the material forming the selected region or regions to temperatures closer to but yet below the temperature level threshold at which therapeutic or other physiological effect occur.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENT

The description that follows is presented to enable one skilled in the art to make and use this invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

Figure 1:
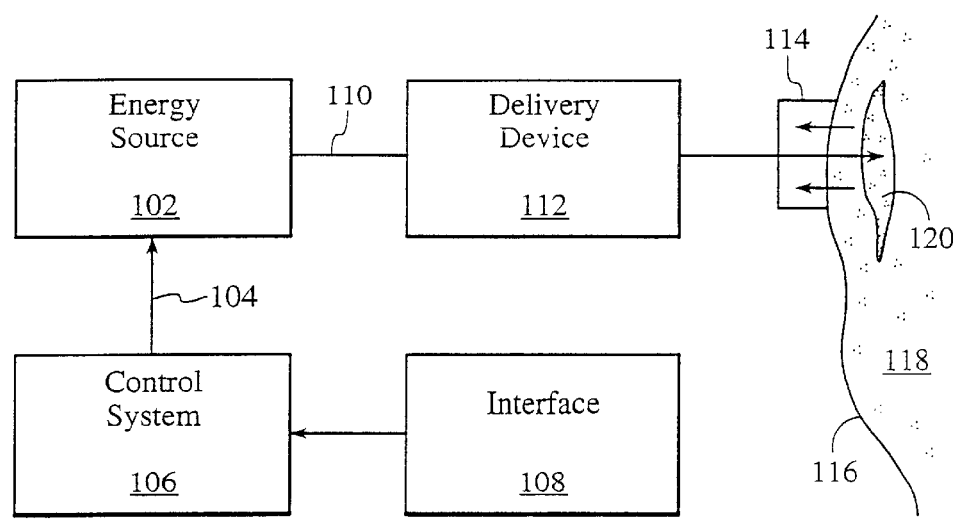
FIG. 1 is a representative schematic block diagram of a preferred embodiment of the system for subsurface heating of material of the present invention.

FIG. 1 is a representative schematic block diagram of a preferred embodiment of the system 100 for subsurface heating of material of the present invention. Operation of energy source 102 to produce energy for delivery by the system 100 is controlled according to control signal 104 from control system 106. Control system 106 includes a physician interface 108 for operating the system. Said interface 108 includes a footswitch for energy delivery, display and interactive and/or menu driven operation utilizing operator input, prompts, etc. Additional energy delivery control interface means shall be known to those skilled in the art.

In a preferred embodiment, energy source 102 is a neodymium doped yttrium-aluminum-garnet (Nd:YAG) laser, energized by a flashlamp or laser diode. Energy source 102 is controlled by control system 106 which comprises the software and electronics to monitor and control the laser system, and interface 108. The beam of laser energy 110 from the energy source 102 is directed into a delivery device 112 which may be an optical fiber, a fiber bundle or articulated arm, etc.

Optional heat sink 114 is provided directly on the surface 116 of material 118. Studies have shown that use of the light energy, produced via laser, flashlamp, filament lamp, etc., with an appropriate heat sink produce an optimum thermal profile in skin tissue for collagen shrinkage and hair removal. It has been shown, for example, that irradiating tissue with the infrared radiation through a surface thermal absorption element or heat sink 114 permits an optimum thermal profile within the target tissue with near physiologic temperature at the surface 116 of the irradiated material 118, thus minimizing surface thermal damage. In the case of collagen shrinkage, this is clearly desirable. Attenuating the surface temperature before irradiation or other delivery of energy to tissue and creating a boundary layer on the skin surface results in selective cooling of the target tissue thus preserving the normal overlying epidermis.

Providing a glass or sapphire tip probe to the surface of the tissue being treated, while transparent to the radiation being delivered to the tissue, will act as an efficient and convenient passive-type heat sink 114 for the surface layers of the skin or for other applications.

Modern instruments to provide dynamic cooling of the surface layers of tissue or other materials are well suited to these applications. A coolant spray can be provided through a handpiece or it could be provided with another separate device. Finally, a connection to a computer and the control system 106 of the energy source 102 will allow the system 100 to utilize electronic or other thermal sensing means and obtain feedback control signals for the handpiece. An optimum cooling strategy might be one that uses a short spurt of cryogenic liquid (e.g., 5–20 ms) to reduce the local temperature in the overlying epidermis, while minimizing attenuation of the filament lamp energy by the boundary layer, followed by post-irradiation cooling spurt that provides cooling or dissipation of the epidermal heat generated by absorption of energy in the non-isotropic skin, optionally containing various pigmentation levels. An appropriate cryogen spray would be tetrafluoroethane, $C_2H_2F_4$, an environmentally compatible, non-toxic, non-flammable freon substitute. In clinical application the distance between the aperture of the spray valve and the skin surface should be maintained at about 20 millimeters.

During a typical dynamic cooling process, the surface of the skin is pre-cooled to as low as 0 degrees Celsius or lower, at a rate fast enough to cool the surface only but not dissipate heat from below about 400–500 microns below the surface. In a preferred embodiment, during the cooling step the target tissue remains at body temperature and is not cooled at all. By applying cooling to the surface of the skin for a short period of time, typically between about 5 and 100 milliseconds and then delivering laser energy, the surface is initially cooled but the target tissue never is. Generally, the surface layer of skin is rapidly cooled. A high rate of cooling will prevent local and vicinal hypothermia and will also tend to have a numbing, anesthetic or analgesic effect. It will be understood that in at least one preferred embodiment of the method of the present invention, since only a relatively very thin outer layer of skin is cooled in a relatively very rapid period of time, laser energy must be applied either instantaneously with termination or dynamic or removal of passive cooling or essentially immediately thereafter. Therefore, upon delivery of laser energy onto the surface and therethrough, the target tissue will be raised to the optimal thermal shrinkage temperature and generally not any higher, in an adequately rapid process, with the surface temperature of the skin remaining unelevated from body temperature, or if elevated at all, not elevated to a temperature which would have any adverse effect on the tissue. Adverse effects of elevated tissue surface temperature include discomfort or pain, thermal denaturing of proteins and necrosis of individual cells at the surface only, or deeper tissue ablation potentially leading to hyperplasia, scarring, or hyperpigmentation, a proliferation of cells formed in response to the induced trauma. In a preferred embodiment of the method of the present invention, cooling and heating are performed in a predetermined timing sequence, optionally with the use of timer circuits and/or other controller means.

Thus, it will be obvious to those skilled in the art that a passive heat sink includes glass or sapphire tip probes, and other types of devices to lay on the surface of the skin. It will also be obvious that a dynamic type of heat sink will refer to those actively cooled by flowing gas or liquid, jets or spurts of coolant such as freon, and other active types of heat exchangers suitable for surface cooling while irradiating sub-surface portions of collagen tissue. U.S. Pat. No. 5,820,626 issued Oct. 13, 1998 to Baumgardner, incorporated herein by reference in its entirety, teaches a cooling laser handpiece with refillable coolant reservoir, and can be utilized as a handpiece for delivery device 112 and heat sink 114.

Figure 1A:
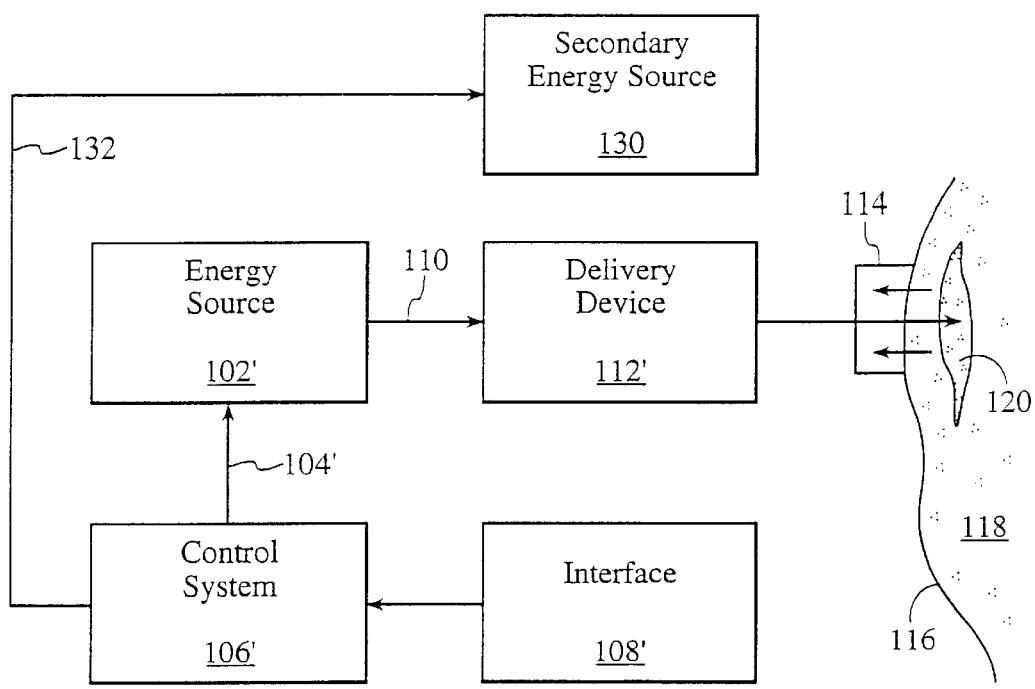
FIG. 1A is a representative schematic block diagram of another preferred embodiment of the system for subsurface heating of material of the present invention.

FIG. 1A is a representative schematic block diagram of another preferred embodiment of the system 100' for sub-surface heating of material of the present invention. As described with respect to FIG. 1, operation of energy source 102' to produce energy for delivery by the system 100' is controlled according to control signal 104' from control system 106'. Control system 106' includes a physician interface 108' for operating the system. Energy 110' from the energy source 102' is directed into a delivery device 112' which may be an optical fiber, a fiber bundle or articulated arm, etc.

A secondary energy source 130 controlled by an independent control signal 132 from control system 108' also communicates energy 134 to delivery device 112'. Said secondary energy source 130 can be incorporated within the primary energy source 102' or can be separate.

Thus, in a preferred embodiment, the energy source 102' comprises a pulsed or continuous wave laser source, a flashlamp or filament lamp, other source of electromagnetic energy including ultrasound infrared, electrical or radiofrequency transmitter or radiator, and is used to provide energy source for the primary therapeutic or other physiological application. The secondary energy source 130 may consist of a similar energy source 102' or may be different. Secondary energy source 130 is utilized to provide the subsurface preheating prior to the delivery of therapeutic or physiologically active amounts of energy from the primary energy source 102'. Therefore, the power rating and/or delivery rate of energy from secondary energy source 130 may be less than that of the primary energy source 102'. In a preferred embodiment, secondary energy source 130 of preheating energy is a diode laser, a filament lamp a gas discharge flashlamp, a source of radio frequency electrical energy, or a microwave source, such that the preheating energy 134 from secondary energy source 130 is delivered to the target portions 120 of material 118 as desired.

Furthermore, it will be understood that in the case of surface cooling via optional heat sink 114, secondary energy source may provide the major share of total amount of energy delivery, i.e., delivery of energy to maintain subsurface target regions 120 within material 118 at an elevated, preheated temperature as well as overcome heat loss from those target regions 120 during surface cooling by active or passive heat sink 114. In this case, primary energy source 102' will provide the necessary additional energy, such as at a different wavelength or some other variation in the type of energy, to effect the desired treatment or other physiological change to the target portions 120 of material 118.

Therefore, it will be understood that the energy utilized for preheating target portions 120 of material below the surface 116, one or more energy sources may be used, and may be controlled independently, both through a common control system 106'. In either case, the system 100 or 100' may comprise wavelength multipliers or dividers, beam splitters, filters, collimators, focusing lenses, gates or gratings, mirrors or other optical and/or electronic and/or electrical devices, and the energy, however originally produced, may be converted from one form to another, such as from electrical to photonic, prior to delivery to the target portions 120 through the surface 116 of the material 118 to be treated.

Figure 2:
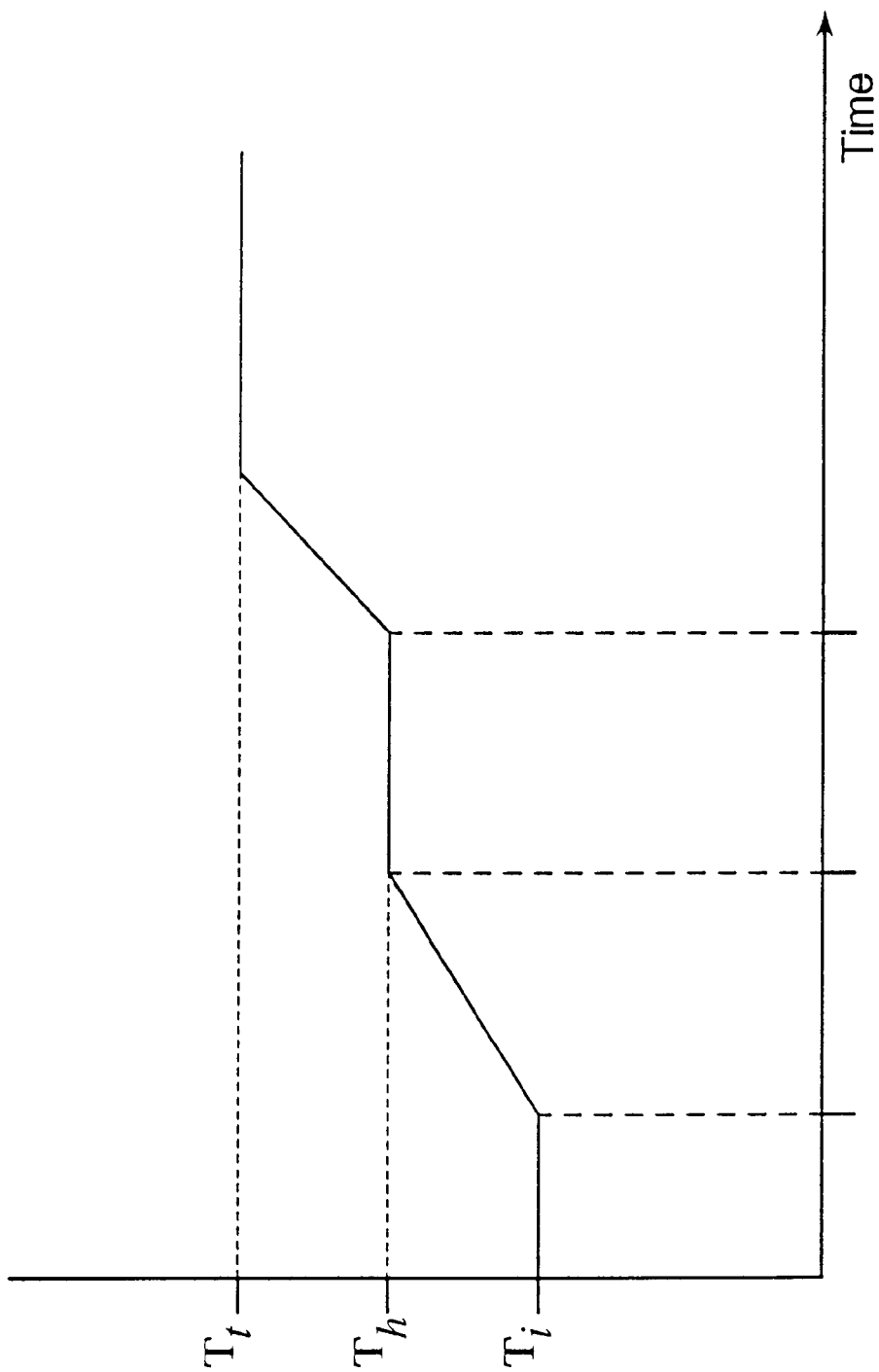
FIG. 2 is a representative plot of the temperature rise of selected material using the system of the present invention such as shown in FIG. 1.

FIG. 2 is a representative plot of the temperature rise of the selected material using the system of the present invention such as shown in FIG. 1. This invention is a method of warming the areas to be treated to a temperature above normal, but below treatment levels in order to reduce the amount of additional pulsed energy needed to treat the target tissue. As mentioned above, tissue is modified or destroyed at a generally fixed and known temperature that is usually independent of the starting, native, resting, natural, ambient temperature of the tissue. It is known that collagen will shrink at approximately 65° C. Most methods of shrinking collagen deliver energy in a pulsed manner to raise the tissue from an initial temperature, such as the normal body temperature of 30° C., all the way to 65° C. at one time. This temperature rise of 35° C. requires energy sources capable of delivering up to 6 joules to elevate a 5 mm diameter spot. The present invention performs this same process in several steps.

In a first step, the target portions of material 120 are raised from their initial, native or body temperatures $T_i$ to a controlled, non destructively heated intermediate level $T_h$, e.g., 40° C., utilizing one of several techniques including incoherent or laser irradiation, radiofrequency waves, microwaves, or contact, such as with warm materials or sprays of heated liquid or gas. The heat capacity of dermatological tissue is relatively linear over this region so the energy needed to provide the second and final temperature rise from $T_h$ to $T_t$, such as about $\Delta 20°$ C., will be only about two thirds, or more or less, of the amount energy need to produce the same end temperature $T_t$ from $T_i$, or about 30° C. ambient or initial temperature. The reduced amount of energy needed for treatment, therefore, provides the opportunity to treat a larger area and to use a smaller and safer device.

A preferred method of pre warming target tissues is to utilize selective techniques that will warm the target area or structure more than surrounding tissues to minimize collateral damage. For example in the treatment of unwanted hair, the target is the hair follicle which can be selectively heated with a range of optical wavelengths which are absorbed only by the melanin in the follicle. An ideal sequence would be:

1. Pre warm 1 to 3 mm into the target tissue or treatment area where the hair follicle is located with electromagnetic radiation of between about 600 and about 1200 um wavelength for approximately one to five seconds until the hair follicles are between about 40° C. and about 50° C.
2. Cool the surface of the skin with a contact plate or dynamic cooling spray for 10 to 1000 milliseconds so as cool only the epidermis and not affect the hair follicle,
3. Irradiate the area with pulsed light of between about 600 and about 1200 nm wavelength that will selectively heat the follicle to the point of damage without affecting the surrounding tissue.

The prewarming or preheating of the target tissue can be done with a continuous source or a series of pulses that are low enough in energy as to act like a continuous source.

Since the treatment portion of the procedure only uses between about ½ and about ⅔ of the energy previously needed to damage hair follicles, such as for hair removal or for stimulation applications, temperature increase in surrounding or non-target tissue or other portions of the epidermis will likewise be reduced by as much as between about ½ and about ⅔ of what would otherwise be expected, thus minimizing the risk of burning, blistering or scarring of the superficial and top layers of skin.

The reduced energy need, therefore, to treat the target tissue, also allows use of the same power filament or other incandescent lamp operated in a pulsed fashion to treat a relatively larger area. This is a significant advantage when treating legs or backs which can take hours to treat using the 5 to 8 mm spot sizes of current systems. This invention will allow, therefore, the use of treatment spot sizes of 33 to 50% more area than possible heretofore.

The method includes treating dermatological tissue using a pulsed, non-coherent light source, such as by pulsing electric current through a filament or other portion of an incandescent lamp at a maximum potential and for a maximum time period. It will be understood that this maximum potential and/or maximum time period for the pulse rate will be determined by the materials and method of construction of the lamp. As is well know, excessive potential or current flow through a filament lamp will have a destructive effect on the lamp and its components, thereby reducing the efficiency of the procedure, and possibly causing destruction of the light source and/or other portions of the device including the lamp housing, as well as a potential cause of injury to a patient or physician.

Figure 3:
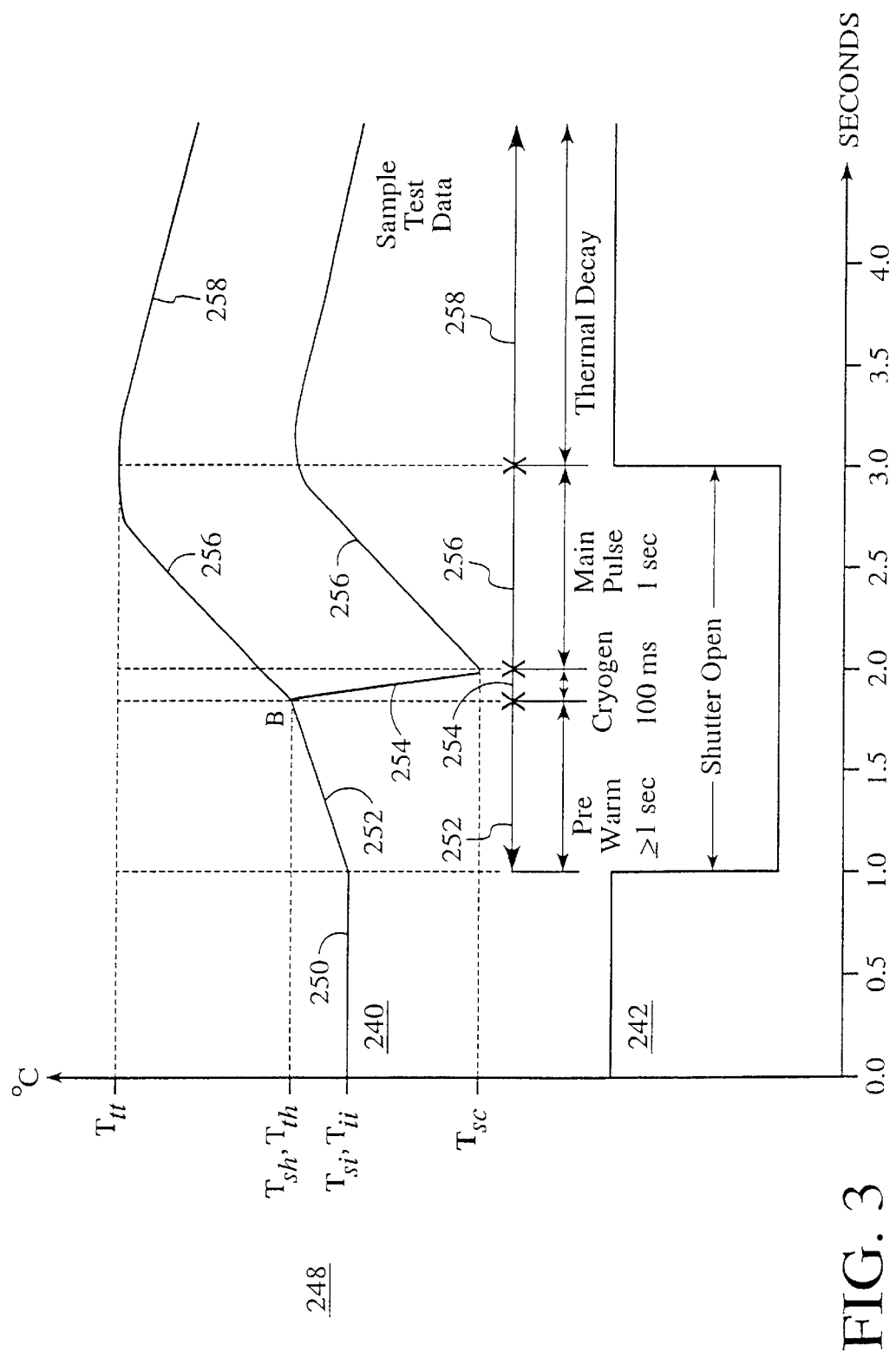
FIG. 3 is a representative plot of the surface temperature and adjacent target portions of material using the system of the present invention such as shown in FIG. 1 with precooling.

FIG. 3 is a representative plot of the surface temperature and adjacent target portions of material using the system of the present invention such as shown in FIG. 1 with precooling. FIG. 3 is representative of treatment of human tissue. The waveforms are representative of oscilloscope-type traces which reproduce signals generated by one or more thermal detectors.

The lower waveform 242 indicates the period of time during which energy is delivered to the material, in this case about 2.0 seconds. On the upper waveform 248, at an initial time 250, temperature of the surface 116 of the material and the target portions 120 are at $T_{si}$ and $T_{ii}$, respectively. The temperature of both the surface and the target portions of material is raised over time period 252 to pre-warmed states at temperature $T_{sh}$ and $T_{th}$. It will be understood that by controlling delivery of energy, the temperature of both the surface as well as the target portions of material can be maintained for any length of time at the pre-warmed temperatures $T_{sh}$ and $T_{th}$.

Trace 240 becomes bifurcated at point B, at which point cryogen spray is initiated and/or at which point delivery of additional energy increases the temperature of the target portions 120 of material 118 above $T_{th}$. Although the temperature of the target portions 120 of material continue to rise upon continued delivery of energy, from $T_{th}$ up to a maximum temperature desired for the course of intended treatment, such as at temperature $T_{tt}$, with initiation of cryogen spray or other coolant, passive or active, the temperature of the warmed surface of the material $T_{sh}$ is maintained at $T_{sh}$ or drops to a lower temperature $T_{sc}$ during time period 254, correlating with a cryogen spray time period of about 100 milliseconds as shown in FIG. 3. The temperature $T_{sc}$ of the cooled surface 120 starts to rise again throughout the remainder of time period 242 during which time energy is delivered, up to some intermediate temperature, between about $T_{sc}$ and about $T_{sh}$.

Thereafter, on termination of delivery of energy, the temperature of both the surface 116 as well as the target portions 120 of material drop through thermal decay time period 258 back down to the baseline temperatures of about $T_{si}$ and about $T_{ii}$, respectively. The cycle shown in FIG. 3 can be repeated to provide treatment of a large target portion of material below broad surfaces areas.

It will be understood that cooling may be initiated before, concurrently with or after initiating delivery of energy to the material. In any case the target portions 120 of material 118 are raised from their initial temperatures at $T_{ii}$ to an intermediate, pre-heated or pre-warmed temperature $T_{th}$, while the temperature of the surface 116 of the material 118 is similarly raised from $T_{si}$ to $T_{sh}$ and is maintained anywhere between $T_{sc}$ and $T_{sh}$. Thereafter, treatment of the target portions 120 of material may take place at any time, by raising the temperature of the target portions 120 of material 118 to treatment temperature $T_{tt}$.

It will be understood that while numerous preferred embodiments of the present invention are presented herein, numerous of the individual elements and functional aspects of the embodiments are similar. Therefore, it will be understood that structural elements of the numerous apparatus disclosed herein having similar or identical function may have like reference numerals associated therewith.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method for treatment of subsurface tissue using a pulsed energy source and delivery system, the method comprising at least the following steps:

preheating both a subsurface target portion of tissue and a non-target surface portion of tissue to a first temperature below a target treatment temperature;

maintaining the subsurface target portion of tissue and non-target surface portion of tissue below the target treatment temperature for a period of time;

subsequently administering a cryogen spray to the non-target surface portion of tissue for a period of time of about 100 milliseconds and delivering pulsed energy with a delivery device to the preheated tissues, wherein the subsequent administration of cryogen spray and delivery of pulsed energy causes the subsurface target portion of tissue to be raised to a target treatment temperature greater than said first temperature while the non-target surface portion of tissue remains at a temperature below the target treatment temperature; and maintaining the delivery of pulsed energy to the tissues such that the non-target surface portion of tissue is maintained at a temperature lower than the target treatment temperature.

2. The method of claim 1 in which the subsurface tissue is vascular tissue.

3. The method of claim 1 in which the subsurface tissue is collagen containing tissue.

4. The method of claim 1 in which the subsurface tissue is cartilage.

5. The method of claim 1 in which the subsurface tissue contains pigment.

* * * * *